(12) United States Patent
Zhou

(10) Patent No.: US 11,554,224 B2
(45) Date of Patent: Jan. 17, 2023

(54) ELECTRONIC ATOMIZING APPARATUS, CONTROL METHOD THEREOF AND POWER SUPPLY ASSEMBLY

(71) Applicant: Shenzhen Smoore Technology Limited, Shenzhen (CN)

(72) Inventor: Jun Zhou, Shenzhen (CN)

(73) Assignee: SHENZHEN SMOORE TECHNOLOGY LIMITED, Shenzhen (CN)

( * ) Notice: Subject to any disclaimer, the term of this patent is extended or adjusted under 35 U.S.C. 154(b) by 448 days.

(21) Appl. No.: 16/850,513

(22) Filed: Apr. 16, 2020

(65) Prior Publication Data

US 2020/0360629 A1 Nov. 19, 2020

(51) Int. Cl.
  *A61M 11/04* (2006.01)
  *A24B 15/16* (2020.01)
  *A61M 15/06* (2006.01)

(52) U.S. Cl.
  CPC ........... *A61M 11/042* (2014.02); *A24B 15/16* (2013.01); *A61M 15/06* (2013.01)

(58) Field of Classification Search
  CPC ..... A61M 11/042; A61M 15/06; A24B 15/16; A24F 40/10; A24F 40/20; A24F 40/30; A24F 40/40; A24F 40/51; A24F 40/60
  See application file for complete search history.

(56) References Cited

U.S. PATENT DOCUMENTS

| | | | |
|---|---|---|---|
| 9,427,022 B2* | 8/2016 | Levin | A24F 40/51 |
| 10,298,225 B1* | 5/2019 | Most | H05B 1/02 |
| 2015/0305409 A1 | 10/2015 | Verleur et al. | |
| 2016/0158782 A1 | 6/2016 | Henry et al. | |
| 2017/0156397 A1* | 6/2017 | Sur | A24F 40/51 |
| 2017/0245552 A1* | 8/2017 | Reevell | H05B 1/0227 |
| 2018/0213844 A1* | 8/2018 | Sur | A24B 15/167 |
| 2021/0023315 A1* | 1/2021 | Goldenberg | A61M 15/06 |

FOREIGN PATENT DOCUMENTS

| | | | |
|---|---|---|---|
| CN | 108697166 A | | 10/2018 |
| CN | 109393565 A | | 3/2019 |
| CN | 109426171 A | | 3/2019 |
| EP | 2875740 A2 | | 5/2015 |
| JP | WO2018025380 A1 | * | 4/2019 |
| WO | WO2013138384 A2 | | 9/2013 |

OTHER PUBLICATIONS

European search report, Application No. EP20172210, dated Sep. 15, 2020.

* cited by examiner

*Primary Examiner* — Marcus E Harcum

(57) ABSTRACT

The present disclosure provides an electronic atomizing apparatus and an atomizer, a power supply assembly, a control method thereof. The electronic atomizing apparatus may include a housing and a heater, a battery, an angle detection mechanism and a processor arranged in the housing. The housing may be configured to define a liquid storage chamber and a mouthpiece. The liquid storage chamber may be configured to storage aerosol-generating liquid and may be arranged between the mouthpiece and the heater. The heater may be configured to be powered by the power supply assembly. The angle detection mechanism may be configured to detect the tilt angle of the electronic atomizing apparatus. The processor may be connected with both the heater and the angle detection mechanism and may be configured to control the heater to stop heating when it is determined that a tilt angle is greater or equal to an angle threshold.

20 Claims, 5 Drawing Sheets

ELECTRONIC ATOMIZING APPARATUS, CONTROL METHOD THEREOF AND POWER SUPPLY ASSEMBLY

CROSS REFERENCE TO RELATED APPLICATION

The present disclosure claims priority to Chinese Patent Application No. 201910409910.8 entitled "ELECTRONIC ATOMIZING APPARATUS, ATOMIZER, POWER SUPPLY ASSEMBLY AND CONTROL METHOD THEREOF" and filed on May 16, 2019, the entire contents of which are incorporated by reference herein.

TECHNICAL FIELD

The present disclosure relates to the field of daily electronic products, and more particular to an electronic atomizing apparatus, a control method thereof, and a power supply assembly.

BACKGROUND

An electronic atomizing apparatus, as an alternative to a cigarette article, is mostly used for smoking cessation. The electronic atomizing apparatus may have a similar appearance and taste to a cigarette, but may not contain harmful components such as tar and suspended particles generally found in conventional cigarettes, and thus could reduce harm to the human body.

The liquid storage chamber in the electronic atomizing apparatus is generally arranged between the mouthpiece and the heater. If the user does not properly operate the electronic atomizing apparatus during use, a potential safety hazard may result. For example, when the electronic atomizing apparatus is inverted, there may be little or no aerosol-generating liquid heated by the heater, resulting in the heater being in a dry burning state, thereby damaging the electronic atomizing apparatus. Further in the dry burning state, harmful substances may be produced and inhaled by the user with the smoke, which could be harmful to the health of the user.

SUMMARY

According to an aspect of the present disclosure, an electronic atomizing apparatus may include: a housing, the housing may be configured to define a liquid storage chamber and a mouthpiece, the liquid storage chamber may be configured to storage aerosol-generating liquid; a heater, arranged in the housing and configured to atomize the aerosol-generating liquid by heating, the liquid storage chamber may be arranged between the mouthpiece and the heater; a battery, arranged in the housing and connected to the heater, and configured to supply power to the heater to atomize by heating; an angle detection mechanism, arranged in the housing, and configured to detect a tilt angle of the electronic atomizing apparatus; a processor, arranged in the housing and connected to the heater and the angle detection mechanism, the processor may be configured to determine whether the tilt angle may be less than the angle threshold, when it is determined that the tilt angle is less than the angle threshold, the processor may control the heater to start heating; when it is determined that the tilt angle is greater or equal to the angle threshold, the processor may control the heater to stop heating.

According to another aspect of the present disclosure, a power supply assembly may include a power supply assembly housing, a battery and a processor arranged in the power supply assembly housing, a heater and an angle detection mechanism are arranged in the electronic atomizing apparatus. The heater, the battery and the angle detection mechanism are all connected with the processor. The angle detection mechanism may be configured to detect a tilt angle of the electronic atomizing apparatus. The processor may be configured to determine whether the tilt angle is less than the angle threshold. When it is determined that the tilt angle is less than the angle threshold, the processor may control the battery to make the heater to start heating. When it is determined that the tilt angle is greater or equal to the angle threshold, the processor may control the battery to make the heater to stop heating.

According to another aspect of the present disclosure, a control method of an electronic atomizing apparatus may include: detecting a tilt angle of an electronic atomizing apparatus; determining whether the tilt angle is less than an angle threshold; controlling a heater to start heating when the tilt angle is less than the angle threshold; controlling the heater to stop heating when the tilt angle is greater or equal to the angle threshold.

BRIEF DESCRIPTION OF THE DRAWINGS

In order to more clearly illustrate the technical solution in embodiments of the present disclosure, the drawings used in the description of the embodiments will be briefly introduced below. Obviously, the drawings in the following description are just some embodiments of the present disclosure. For those of ordinary skill in the art, other drawings could be obtained according to these drawings without paying creative works.

DETAILED DESCRIPTION

The technical solution in embodiments of the present disclosure will be clearly and thoroughly described with reference to the drawings in embodiments of the present disclosure. Obviously, the described embodiments are merely part of the embodiments of the present disclosure, but not all of them. Based on the embodiments in the present disclosure, all other embodiments obtained by a person of ordinary skill in the art without creative works shall fall within the protection scope of the present disclosure.

Figure 1:
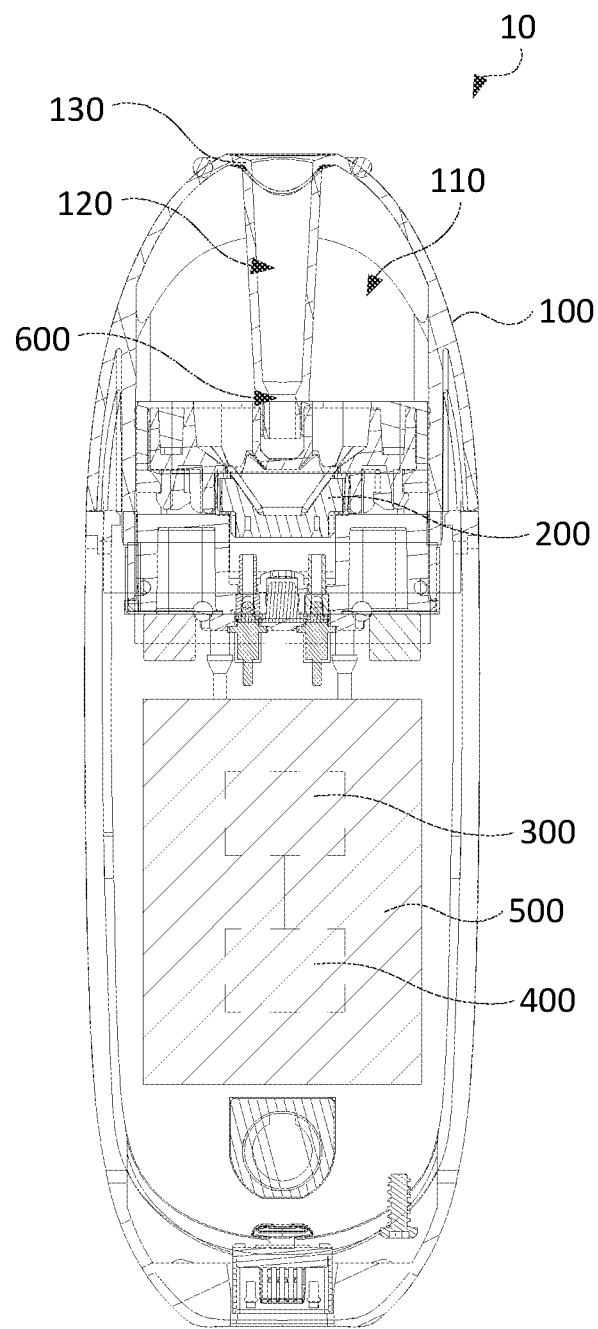
FIG. 1 is a sectional view of an electronic atomizing apparatus according to an embodiment of the present disclosure.

Referring to FIG. 1, an electronic atomizing apparatus 10 according to one embodiment of the present disclosure may include a housing 100, a heater 200, an angle detection mechanism 300, a processor 400 and a battery 500. The housing 100 may be configured to define a liquid storage chamber 110, an air flow channel 120 and a mouthpiece 130. The liquid storage chamber 110 may communicate with the airflow channel 120 through the heater 200. The airflow channel 120 may communicate with the atmosphere through the mouthpiece 130. The heater 200, the angle detection mechanism 300, the processor 400 and the battery 500 may each be arranged in the housing 100. The liquid storage chamber 110 may be arranged between the mouthpiece 130 and the heater 200 and could be configured to storage the aerosol-generating liquid. The processor 400 may be connected to the heater 200 and the angle detection mechanism 300. The heater 200 may be configured to atomize the aerosol-generating liquid (not shown in the figure) in the liquid storage chamber 110 by heating. The battery 500 may be connected to the heater 200, and may be configured to supply power to the heater 200 for atomizing by heating. The angle detection mechanism 300 may be configured to detect the tilt angle of the electronic atomizing apparatus 10. The processor 400 may be configured to determine whether the tilt angle is less than an angle threshold. When it is determined that the tilt angle is less than the angle threshold, the processor 400 would control the heater 200 to start heating. When it is determined that the tilt angle is greater or equal to the angle threshold, the processor 400 would control the heater 200 to stop heating.

In the embodiments of the present disclosure, the angle detection mechanism may be arranged in the electronic atomizing apparatus to detect the tilt angle of the electronic atomizing apparatus. When it is determined that the tilt angle is less than the angle threshold, the processor can control the heater to stop heating, thereby avoiding dry burning when the electronic atomizing apparatus is tilted, and preventing the components of the electronic atomizing apparatus from being damaged. Moreover, production of harmful substances could be prevented due to the dry burning of the aerosol-generating liquid, thereby reducing harm to the health of the user.

In the present embodiment, the angle detection mechanism 300 and the processor 400 may both be arranged on the battery 500. In other embodiments, the angle detection mechanism may also be directly arranged in other locations of the housing 100. For example, the angle detection mechanism may be arranged in a location adjacent to the heater 200, or at a side of the battery 500 away from the heater 200, which is not limited herein.

In the present embodiment, the angle detection mechanism 300 may be an angle sensor configured to directly detect the tilt angle of the electronic atomizing apparatus 10, specifically a gravity sensor or a tilt sensor. The tilt angle of the electronic atomizing apparatus 10 could be detected by the angle sensor more accurately, and the angle sensor may occupy a small space, which could facilitate the miniaturization of the electronic atomizing apparatus 10.

Figure 2:
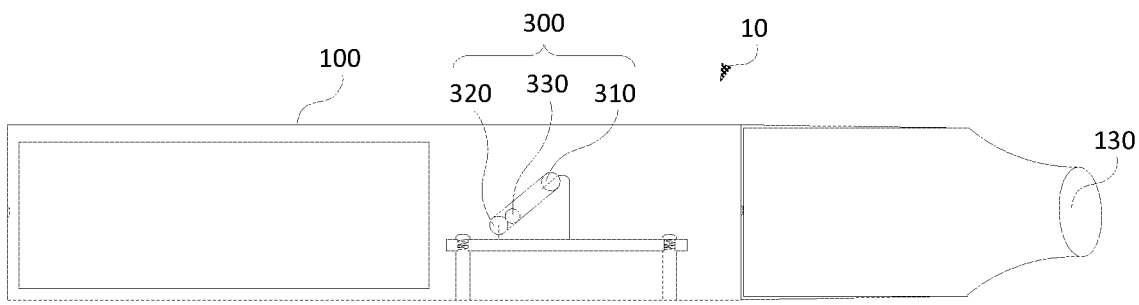
FIG. 2 is a schematic structural diagram of an electronic atomizing apparatus according to another embodiment of the present disclosure.

Referring to FIG. 2 together, in another embodiment, the angle detection mechanism 300 may be a ball switch. The ball switch may include a conducting terminal 310, a disconnecting terminal 320, and a ball 330 arranged between the conducting terminal 310 and the disconnecting terminal 320. The ball 330 may be configured to abut the conducting terminal 310 and the disconnecting terminal 320 respectively.

In the present embodiment, when the tilt angle of the electronic atomizing apparatus 10 is less than the angle threshold, the ball 330 would roll to abut the disconnecting terminal 320. When the tilt angle of the electronic atomizing apparatus 10 is greater or equal to the angle threshold, the ball 330 would roll to abut the conducting terminal 310. The processor 400 may also be configured to detect the abutment between the ball 330 and the conducting terminal 310 or the abutment between the ball 330 and the disconnecting terminal 320. If the abutment between the ball 330 and the disconnecting terminal 320 is detected, the processor 400 would control the heater 200 to start heating; and if the abutment between the ball 330 and the conducting terminal 310 is detected, the processor 400 would control the heater 200 to stop heating.

In the present embodiment, the electronic atomizing apparatus 10 may further include an alerter (not shown in the figures), which may be communicatively connected to the processor 400, and may be configured to alert the user of a wrong operation manner of the electronic atomizing apparatus 10 when the tilt angle of the electronic atomizing apparatus 10 is greater or equal to the angle threshold. The alerter may be an alerting light or an audio alert and so on.

Figure 3:
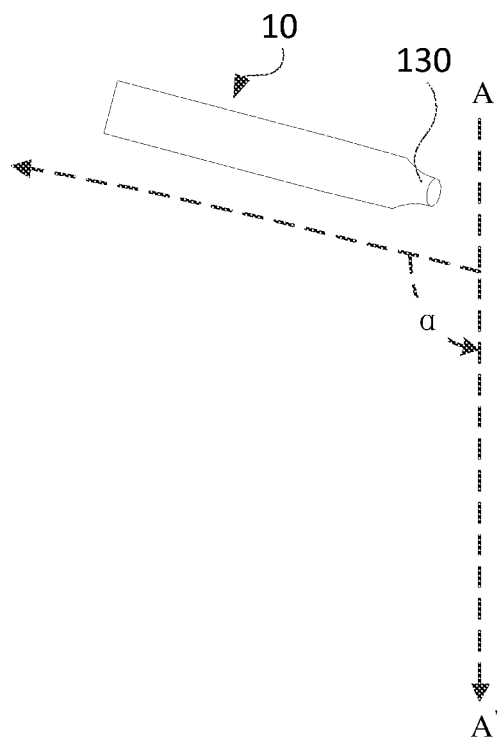
FIG. 3 is a schematic diagram of an electronic atomizing apparatus of the present disclosure in a tilted state.

Referring also to FIG. 3, the tilt angle α is the angle between the opposite direction of orientation of the mouthpiece 130 of the electronic atomizing apparatus 10 and the vertical downward direction AA', and the angle threshold can be from 90° to 150°, such as 90°, 120°, or 150°.

In other embodiments, multiple angle thresholds may also be set, such as a first angle threshold and a second angle threshold are set. The first angle threshold may be less than the second angle threshold. When the tilt angle of the electronic atomizing apparatus 10 is greater or equal to the first angle threshold and less than the second angle threshold, the processor 400 would control the heater 200 to reduce its heating power. When the tilt angle of the electronic atomizing apparatus 10 is greater or equal to the angle threshold, the processor 400 would control the heater 200 to stop heating. The first angle threshold may be from 90° to 120°, such as 90°, 100°, or 120°; the second angle threshold may be from 120° to 150°, such as 120°, 140°, or 150°.

In other embodiments, three or more than three angle thresholds could be set, and multiple heating power stages could be correspondingly set.

In the present embodiment, multiple angle thresholds are set, thus the electronic atomizing apparatus 10 could have different heating powers at different tilt angles, so that when the electronic atomizing apparatus 10 is tilted, overheating due to the amount of the aerosol-generating liquid heated by the heater being too low could thereby be avoided.

In the present embodiment, the electronic atomizing apparatus 10 further includes a trigger switch (not shown in the figures). The trigger switch may be communicatively connected to the processor 400. The trigger switch may be configured to receive a trigger instruction and send the trigger instruction to the processor 400. The processor 400 may control the heater 100 to start heating upon receiving the trigger instruction and may receive the tilt angle information detected by the angle detection mechanism 300.

In the present embodiment, a choke switch 600 may be further arranged in the airflow channel 120. The choke switch 600 may be configured to open the airflow channel 120 when the tilt angle is less than the angle threshold, and close the airflow channel 120 when the tilt angle is greater than or equal to the angle threshold.

In other embodiments, the choke switch may also be arranged in the liquid storage chamber 110, which is not limited herein.

In the present embodiment, the tilt angle of the electronic atomizing apparatus may be detected by the angle sensor or the ball switch, and the accuracy is higher. By arranging an alerter, the user could be timely warned to correct the operation manner of the electronic atomizing apparatus, thereby prolonging the service life of the electronic atomizing apparatus. By arranging the angle detection mechanism and the processor on a battery with larger cross sectional area, the structure of the electronic atomizing apparatus can be more stable, the inner space of the electronic atomizing apparatus can be more fully used, and the structure can be more compact. By arranging a choke switch, leakage of the aerosol-generating liquid from the mouthpiece when the electronic atomizing apparatus is inverted can be avoided, thus avoiding the waste of the aerosol-generating liquid and the contamination of the environment.

Figure 4:
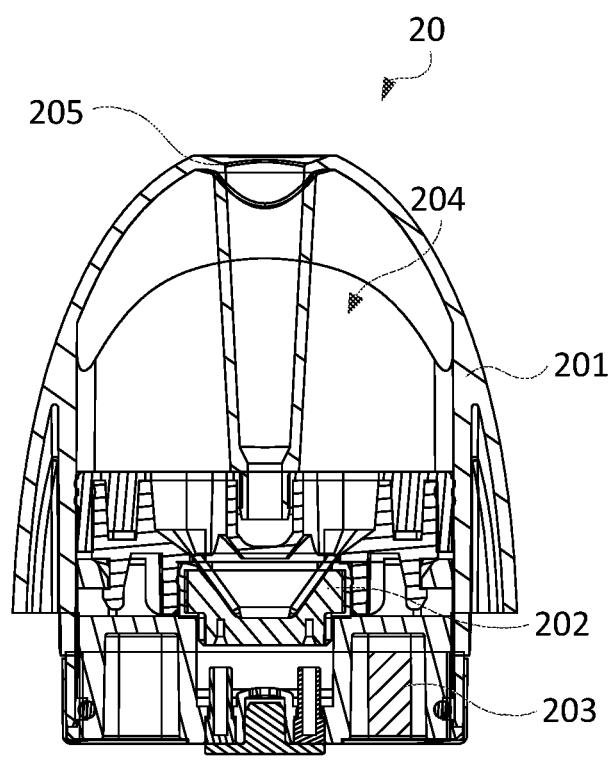
FIG. 4 is a sectional view of an atomizer used in an electronic atomizing apparatus according to an embodiment of the present disclosure.

Referring to FIG. 4, an atomizer 20 configured to be used in an electronic atomizing apparatus according to an embodiment of the present disclosure may include an atomizer housing 201, a heater 202 and an angle detection mechanism 203. The atomizer housing 201 may be configured to define a liquid storage chamber 204 and a mouthpiece 205. The liquid storage chamber 204 may be configured to storage aerosol-generating liquid. The heater 202 may be arranged in the atomizer housing 201, powered by a power supply assembly (not shown in the figures) of the electronic atomizing apparatus, and configured to atomize the aerosol-generating liquid by heating. The liquid storage chamber 204 may be arranged between the mouthpiece 205 and the heater 202. The angle detection mechanism 203 may be arranged in the atomizer housing 201 and may be configured to detect the tilt angle of the electronic atomizing apparatus. The heater 202 and the angle detection mechanism 203 may also be configured to connect with the processor of the electronic atomizing apparatus, such that the processor could determine whether the tilt angle is less than the angle threshold. When it is determined that the tilt angle is less than the angle threshold, the processor would control the heater 202 to start heating. When it is determined that the tilt angle is greater or equal to the angle threshold, the processor could control the heater 202 to stop heating.

In the present embodiment, the angle detection mechanism 203 may be an angle sensor or a ball switch. Specifically, referring to the foregoing embodiments of the electronic atomizing apparatus 10, the details are not described herein again.

In the embodiments of the present disclosure, an angle detection mechanism may be arranged on the atomizer of the electronic atomizing apparatus to detect the tilt angle of the electronic atomizing apparatus. When it is determined that the tilt angle is less than the angle threshold, the processor of the electronic atomizing apparatus could control the heater to stop heating. Thereby dry burning could be avoided when the electronic atomizing apparatus is tilted, and the components of the electronic atomizing apparatus could be effectively protected from damage, harmful substances could be prevented from being produced due to the dry burning of the aerosol-generating liquid, and the harm to the user's health could be reduced.

Figure 5:
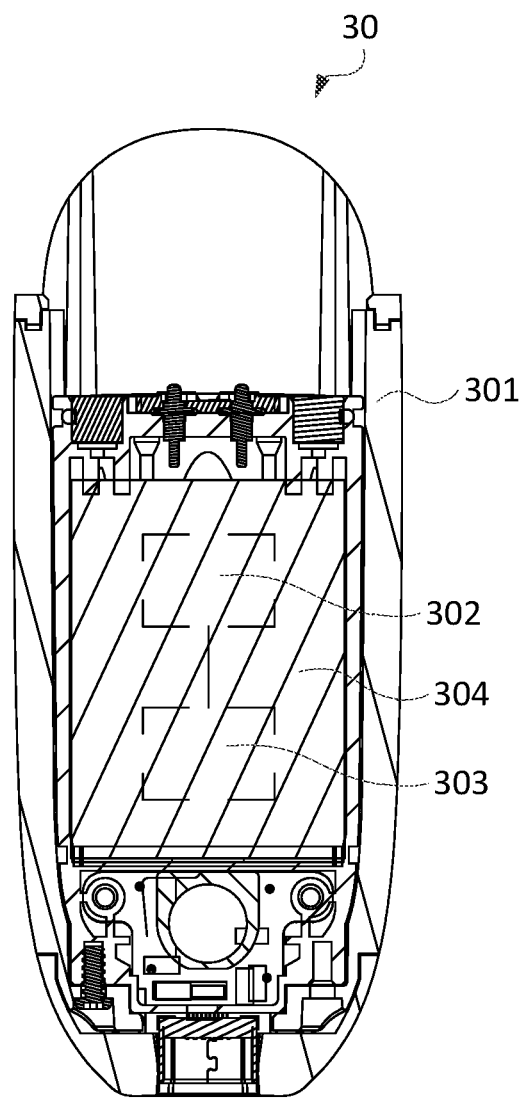
FIG. 5 is a sectional view of a power supply assembly used in an electronic atomizing apparatus according to an embodiment of the present disclosure.

Referring to FIG. 5, the power supply assembly 30 configured to be used in the electronic atomizing apparatus according to one embodiment of the present disclosure may include a power supply assembly housing 301, a processor 303 and a battery 304 arranged in the power supply assembly housing 301. A heater (not shown in the figures) and an angle detection mechanism 302 may be arranged in the electronic atomizing apparatus. The heater, the battery 304 and the angle detection mechanism 302 may all be connected to the processor 303. The angle detection mechanism 302 may be configured to detect the tilt angle of the electronic atomizing apparatus. The processor 303 may be configured to determine whether the tilt angle is less than the angle threshold. When it is determined that the tilt angle is less than the angle threshold, the processor 303 would control the battery 304 so that the heater could start heating. When it is determined that the tilt angle is greater or equal to the angle threshold, the processor 303 would control the battery 304 so that the heater could stop heating.

In the present embodiment, the angle detection mechanism 302 is arranged in the power supply assembly housing 301. In other embodiments, the angle detection mechanism could also be arranged in the atomizer of the electronic atomizing apparatus. When the power supply assembly 30 and the atomizer are assembled to create an electronic atomizing apparatus, the processor 303 of the power supply assembly 30 and the angle detection mechanism of the atomizer could be coupled to control the heater depending on the tilt angle detected by the angle detection mechanism.

In the present embodiment, the angle detection mechanism 302 may be an angle sensor or a ball switch. Specifically, referring to the foregoing embodiments of the electronic atomizing apparatus 10, and details are not described herein again.

In the embodiments of the present disclosure, an angle detection mechanism may be arranged on the power supply assembly of the electronic atomizing apparatus to detect the tilt angle of the electronic atomizing apparatus. When it is determined that the tilt angle is less than the angle threshold, the processor could control the heater to stop heating, thereby dry burning is avoided when the electronic atomizing apparatus is tilted, and the components of the electronic atomizing apparatus is effectively protected from being damaged, harmful substances are prevented from being produced due to the dry burning of the aerosol-generating liquid, and the harm to the user's health is reduced.

Figure 6:
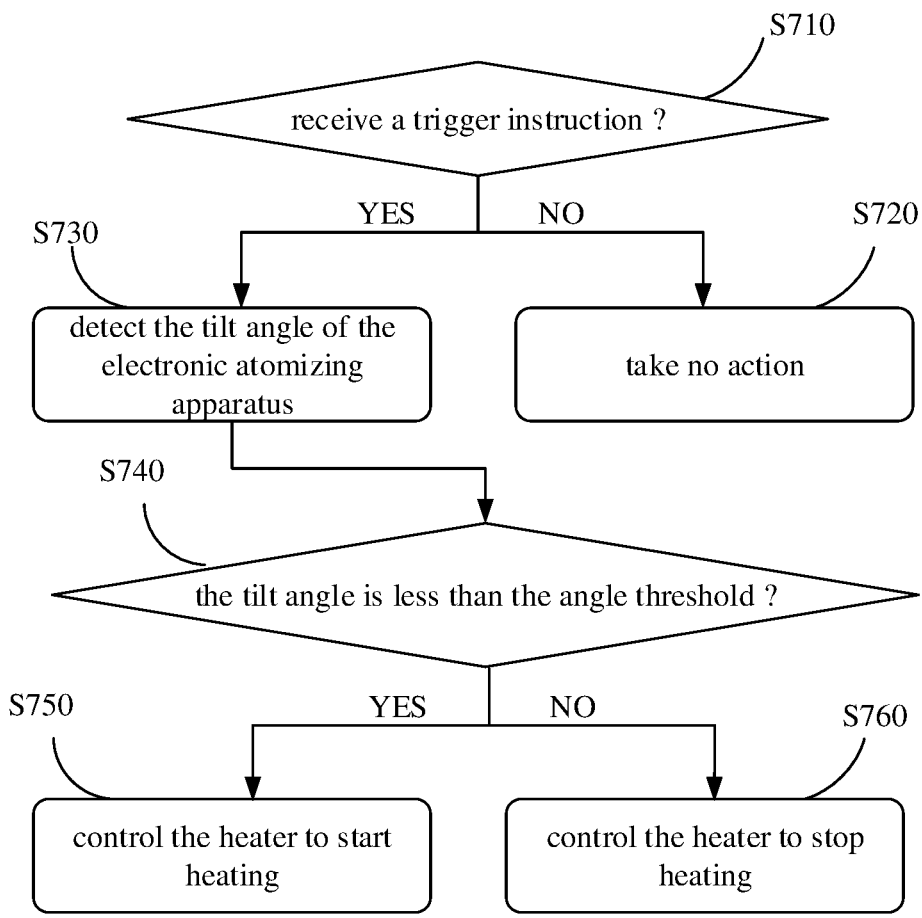
FIG. 6 is a schematic flowchart of a control method of an electronic atomizing apparatus according to an embodiment of the present disclosure.

Referring to FIG. 6, a control method of the electronic atomizing apparatus according to an embodiment of the present disclosure may include the following operations.

Operation S710, a determination is made about whether a trigger instruction is received.

In the present embodiment, the trigger instruction could be triggered by depressing a button or by voice command and so on.

Operation S720, when no trigger instruction is received, then no action is taken.

Operation S730, when a trigger instruction is received, then the tilt angle of the electronic atomizing apparatus is detected.

In the present embodiment, the tilt angle of the electronic atomizing apparatus may be detected by an angle detection mechanism. The angle detection mechanism could be an angle sensor or a ball switch and so on.

Operation S740, a determination is made about whether the tilt angle is less than the angle threshold.

In the present embodiment, the tilt angle may be the angle between the opposite direction of the orientation of the mouthpiece of the electronic atomizing apparatus and the vertical downward direction, and the angle threshold is from 90° to 150°.

Operation S750, when the tilt angle is less than the angle threshold, then the heater is controlled to start heating.

Operation S760, when the tilt angle is greater or equal to the angle threshold, then the heater is controlled to stop heating.

Specifically, for the structure of the electronic atomizing apparatus for implementing the control method, please refer to the foregoing embodiments of electronic atomizing apparatus, and details are not described herein again.

In the embodiments of the present disclosure, an angle detection mechanism may be arranged in the electronic atomizing apparatus to detect the tilt angle of the electronic atomizing apparatus. When it is determined that the tilt angle is less than the angle threshold, the processor could control the heater to stop heating, thereby dry burning could be avoided when the electronic atomizing apparatus is tilted, and the components of the electronic atomizing apparatus could be effectively protected from being damaged, harmful substances could be prevented from being produced due to the dry burning of the aerosol-generating liquid, and the harm to the user's health could be reduced.

The above is only an implementation of the present disclosure and does not therefore limit the patent scope of the present disclosure. Any equivalent structure or equivalent process change made using the content of the present disclosure and the drawings, or directly or indirectly used in other related technical fields are included in the patent protection scope of the present disclosure.

What is claimed is:

1. An electronic atomizing apparatus, comprising:
   a housing, configured to define a liquid storage chamber and a mouthpiece, the liquid storage chamber is configured to storage aerosol-generating liquid;
   a heater, arranged in the housing and configured to atomize the aerosol-generating liquid by heating, the liquid storage chamber is arranged between the mouthpiece and the heater;
   a battery, arranged in the housing and connected to the heater, and configured to supply power to the heater for heating;
   an angle detection mechanism, arranged in the housing, and configured to detect a tilt angle of the electronic atomizing apparatus; and
   a processor, arranged in the housing and connected to the heater and the angle detection mechanism, the processor is configured to determine whether the tilt angle is less than an angle threshold, when it is determined that the tilt angle is less than the angle threshold, the processor controls the heater to start heating; when it is determined that the tilt angle is greater or equal to the angle threshold, the processor controls the heater to stop heating.

2. The electronic atomizing apparatus according to claim 1, wherein the angle detection mechanism is an angle sensor.

3. The electronic atomizing apparatus according to claim 1, wherein the angle detection mechanism is a ball switch, the ball switch comprises a conducting terminal, a disconnecting terminal and a ball arranged between the conducting terminal and the disconnecting terminal, the ball is configured to abut the conducting terminal and the disconnecting terminal respectively.

4. The electronic atomizing apparatus according to claim 3, wherein when the tilt angle of the electronic atomizing apparatus is less than the angle threshold, the ball rolls to abut the disconnecting terminal; when the tilt angle of the electronic atomizing apparatus is greater or equal to the angle threshold, the ball rolls to abut the conducting terminal.

5. The electronic atomizing apparatus according to claim 4, wherein the processor is further configured to detect the abutment between the ball and the conducting terminal, and detect the abutment between the ball and the disconnecting terminal, when the abutment between the ball and the disconnecting terminal is detected, the processor controls the heater to start heating; when the abutment between the ball and the conducting terminal is detected, the processor controls the heater to stop heating.

6. The electronic atomizing apparatus according to claim 1, wherein the tilt angle is the angle between the opposite direction of the orientation of the mouthpiece of the electronic atomizing apparatus and the vertical downward direction, the angle threshold is from 90° to 150°.

7. The electronic atomizing apparatus according to claim 1, wherein the electronic atomizing apparatus further comprises a trigger switch, the trigger switch is connected to the processor, the trigger switch is configured to receive a trigger instruction and send the trigger instruction to the processor.

8. The electronic atomizing apparatus according to claim 1, wherein the housing further defines an airflow channel, the liquid storage chamber communicates with the airflow channel through the heater, the airflow channel communicates with the atmosphere through the mouthpiece, a choke switch is arranged in the airflow channel or the liquid storage chamber, the choke switch is configured to open the airflow channel when the tilt angle is less than the angle threshold, and close the airflow channel when the tilt angle is greater or equal to the angle threshold.

9. The electronic atomizing apparatus according to claim 1, wherein the housing comprises an atomizer housing and a power supply assembly housing, the atomizer housing is configured to define the liquid storage chamber and the mouthpiece, the battery is arranged in the power supply assembly housing, the angle detection mechanism is arranged in the atomizer housing.

10. A power supply assembly of an electronic atomizing apparatus, wherein the power supply assembly comprises a power supply assembly housing, a battery and a processor arranged in the power supply assembly housing; a heater and an angle detection mechanism are arranged in the electronic atomizing apparatus, the heater, the battery and the angle detection mechanism are all connected with the processor, the angle detection mechanism is configured to detect a tilt angle of the electronic atomizing apparatus, the processor is configured to determine whether the tilt angle is less than an angle threshold, when it is determined that the tilt angle is less than the angle threshold, the processor controls the battery to make the heater to start heating; when it is determined that the tilt angle is greater or equal to the angle threshold, the processor controls the battery to make the heater to stop heating.

11. The power supply assembly according to claim 10, wherein the angle detection mechanism is arranged in the power supply assembly housing.

12. The power supply assembly according to claim 10, wherein the angle detection mechanism is an angle sensor.

13. The power supply assembly according to claim 10, wherein the angle detection mechanism is a ball switch, the ball switch comprises a conducting terminal, a disconnecting terminal and a ball arranged between the conducting terminal and the disconnecting terminal, the ball is configured to abut the conducting terminal and the disconnecting terminal respectively.

14. The power supply assembly according to claim 13, wherein when the tilt angle of the electronic atomizing apparatus is less than the angle threshold, the ball rolls to abut the disconnecting terminal; when the tilt angle of the electronic atomizing apparatus is greater or equal to the angle threshold, the ball rolls to abut the conducting terminal.

15. The power supply assembly according to claim 14, wherein the processor is further configured to detect the abutment between the ball and the conducting terminal, and detect the abutment between the ball and the disconnecting terminal, when the abutment between the ball and the disconnecting terminal is detected, the processor controls the heater to start heating; when the abutment between the ball and the conducting terminal is detected, the processor controls the heater to stop heating.

16. The power supply assembly according to claim 10, wherein the tilt angle is the angle between the opposite direction of the orientation of the mouthpiece of the electronic atomizing apparatus and the vertical downward direction, the angle threshold is from 90° to 150°.

17. A control method of an electronic atomizing apparatus, comprising:

detecting a tilt angle of the electronic atomizing apparatus;

determining whether the tilt angle is less than an angle threshold;

controlling a heater to start heating when the tilt angle is less than the angle threshold; and controlling the heater to stop heating when the tilt angle is greater or equal to the angle threshold.

18. The control method according to claim 17, wherein before the detecting a tilt angle of the electronic atomizing apparatus, the control method further comprises:

determining whether a trigger instruction is received;

detecting the tilt angle of the electronic atomizing apparatus if a trigger instruction is received; and taking no action if no trigger instruction is received.

19. The control method according to claim 17, wherein the tilt angle of the electronic atomizing apparatus is detected by an angle detection mechanism, the angle detection mechanism is an angle sensor or a ball switch.

20. The control method according to claim 17, wherein the tilt angle is an angle between the opposite direction of the orientation of the mouthpiece of the electronic atomizing apparatus and the vertical downward direction, the angle threshold is from 90° to 150°.

\* \* \* \* \*

UNITED STATES PATENT AND TRADEMARK OFFICE
CERTIFICATE OF CORRECTION

| | |
|---|---|
| PATENT NO. | : 11,554,224 B2 |
| APPLICATION NO. | : 16/850513 |
| DATED | : January 17, 2023 |
| INVENTOR(S) | : Jun Zhou |

It is certified that error appears in the above-identified patent and that said Letters Patent is hereby corrected as shown below:

On the Title Page

Column 1 Add Foreign Application Priority Data, Item (30), as follows:
May 16, 2019 (CN) ................................. 201910409910

Signed and Sealed this
Eighteenth Day of June, 2024

Katherine Kelly Vidal
*Director of the United States Patent and Trademark Office*